United States Patent [19]
Berg

[11] Patent Number: 5,123,922
[45] Date of Patent: Jun. 23, 1992

[54] SPEAKING TUBE
[75] Inventor: Nicholas J. Berg, Canton, Mass.
[73] Assignee: Brigham and Women's Hospital, Boston, Mass.
[21] Appl. No.: 632,001
[22] Filed: Dec. 21, 1990
[51] Int. Cl.⁵ .............................................. A61F 2/20
[52] U.S. Cl. ................................... 623/9; 128/207.16
[58] Field of Search .......... 623/9; 128/207.15, 207.16, 128/207.29

[56] References Cited

U.S. PATENT DOCUMENTS

| | | | |
|---|---|---|---|
| 2,198,241 | 4/1940 | Brehm | 623/9 |
| 4,183,102 | 1/1980 | Guiset | 623/1 |
| 4,272,647 | 6/1981 | Veit et al. | 381/70 |
| 4,596,579 | 6/1986 | Pruitt | 623/9 |
| 4,809,693 | 3/1989 | Rangoni et al. | 128/207.16 |

FOREIGN PATENT DOCUMENTS

| | | | |
|---|---|---|---|
| 0078685 | 5/1983 | European Pat. Off. | |
| 2513113 | 3/1983 | France | 623/9 |

Primary Examiner—Randall L. Green
Assistant Examiner—D. Willse
Attorney, Agent, or Firm—Sterne, Kessler, Goldstein & Fox

[57] ABSTRACT

The present invention relates to a prosthetic device and more particularly to a tracheal speaking tube which is received within the stoma of a laryngectomee to assist in the creation of speech. The device includes a tube, an air flow altering device and a vibrating device, the vibrations of which cause an internal wall of the esophagus to vibrate to allow the laryngectomee to form speech.

23 Claims, 5 Drawing Sheets

SPEAKING TUBE

FIELD OF THE INVENTION

This invention relates to a prosthetic device and more particularly to a prosthetic device or tube which is fitted within the tracheostoma of a laryngectomee to assist in the creation of esophageal speech.

BACKGROUND OF THE INVENTION

Following a standard laryngectomy procedure, the recovering laryngectomee is presented with several speech techniques for developing a speaking voice. Such natural techniques include the buccal, pharyngeal and esophageal speech techniques.

The buccal speech technique involves developing sound by squeezing air within the mouth between the cheeks, tongue and palate to create a form of speech. Pharyngeal speech is created by trapping air in the back of the throat with the base of the tongue or against the soft or hard palate. However, both the buccal speech and pharyngeal speech techniques create forms of speech which are incomprehensible.

The laryngectomee creates esophageal speech by injecting air into the upper esophagus to produce a sound which can be formed into normal speech. Unfortunately for the recovering laryngectomee, esophageal speech is often difficult and time consuming to learn.

Electronic or mechanical speech aids (or artificial larynxes) are other options which are available to the rehabilitating laryngectomee. Although existing mechanical and electronic speaking devices are an acceptable substitute for the human voice, they tend to create a speaking tone which is considered to be unnatural and often requires the use of the laryngectomee's hands or the creation of a fistula between the tracheostoma and the pharynx for surgical implantation of the device. Furthermore, some mechanical devices are not operative in the absence of the vocal cords.

These mechanical and electronic speaking devices are well known in the prior art. One example of a mechanical speaking device is found in the Rangoni, et al. patent (U.S. Pat. No. 4,809,693) which discloses a tracheal cannula fitted with a mechanically operated valve to direct air over the vocal cords to produce speech. Obviously, this device is of no service to the patient who has undergone a total laryngectomy where the vocal cords have been removed.

Another example is the Blom, et al. patent document (European Patent Application 0 078 685) which discloses a tracheal valve having a valve assembly for supporting a flexible and lightweight diaphragm. During exhalation, the diaphragm extends to close the valve directing air to the larynx or to an internal voice prosthesis. However, the Blom, et al. device is only operable in the presence of the vocal cords or in combination with a separate voice prosthesis which is received within a fistula. Thus, if the vocal cords of the laryngectomee are not present, the Blom, et al. device requires additional surgery to implant a voice prosthesis.

One example of an electronic speech apparatus is disclosed in U.S. Pat. No. 4,272,647 to Veit, et al. The Veit, et al. patent discloses a speech aid apparatus for laryngectomees which when held against the throat generates sound in the cavity of the mouth and pharynx. By using normal speaking movements, these sounds may be shaped into comprehensible speech. However, one disadvantage of the Veit, et al. device includes constant use of the laryngectomee's hands to create speech. If the laryngectomee's hands are otherwise occupied, speech is not possible utilizing the Veit, et al. device.

Thus, it is an object of the present invention to overcome the disadvantages of the speaking devices described above. The present invention is a tracheal speaking tube which is received within the stoma of a laryngectomee to assist in the creation of speech. The device includes an air flow altering means and an internal vibrating means which is disposed upon the upper interior portion of the tube. The vibrating device may be breath-powered or electro-mechanical. In the present invention, the laryngectomee initiates speech by exhaling forcefully to close the air flow altering means which is located within the speaking tube. Air, trapped within the speaking tube, is directed to the vibrating device which creates vibrations which are then transported to the upper wall of the stoma. The vibrations travel through the tissue of the neck to vibrate the walls of the esophagus. As the walls of the esophagus vibrate, speech is created using normal oral, labial and glossal articulation. Thus, the present invention allows the creation of natural comprehensible speech by using the walls of the esophagus as opposed to an artificial larynx. Because the laryngectomee is able to control the production of speech as he did preoperatively with breath control and normal articulation, phrasing is natural.

The present invention is also advantageous over the prior art because it does not require the use of the laryngectomee's hands or additional surgery to implant a voice prosthesis. Using the present device, the laryngectomee is able to communicate while engaging in other activities which may require use of the hands. Most importantly, the present invention is an integral device which is easily inserted within the tracheostoma of the laryngectomee to assist in the creation of speech with little learning difficulty.

Furthermore, the device of the present invention is easily cleansed of pulmonary secretions due to the provision of a removable inner cannula. Lastly, the internal elements of the speaking tube or inner cannula are streamlined to facilitate normal breathing and the entire device is easily concealable.

SUMMARY OF THE INVENTION

In accordance with the objectives as described above, the present invention is a device for creating speech in a laryngectomee comprising a tube received within the trachea of the laryngectomee; a vibrating means positioned within the tube for creating vibrations and an air flow altering means which is received within the tube for altering the flow of air during exhalation by the laryngectomee. The air flow altering means is positionable between an open position, wherein the flow of air is directed outside the body, and a closed position, wherein the flow of air is directed to the vibrating means. When the flow of air is directed to the vibrating means, the vibrations produced by the vibrating means causes an internal wall of the esophagus to vibrate which allows the laryngectomee to form speech. The tube may be constructed of stainless steel. The air flow altering means may include a flap and the vibrating means may be selected from a group comprised of a reed, a spring, a transducer and a narrow valve. The device may further include a cannula which is removably received within the tube and the air flow altering means and vibrating means may be disposed upon the cannula. The device may also include a sound transporting means for transporting the vibrations to the internal wall of the laryngectomee's esophagus and the sound transporting means may include a sound port. The device may further comprise a securing means for securing the tube within the laryngectomee's trachea and the securing means may include an inflatable cuff which may be inflated by an external pump.

Furthermore, the present invention is a device for creating speech in a laryngectomee comprising a tube received within the trachea of the laryngectomee; a means for vibrating an internal wall of the esophagus which is received within the tube; an air flow altering means received within the tube which is positionable between an open position and a closed position and a breath activated device which is also received within the tube. The breath activated device activates the vibrating means when the air flow altering means is in a closed position, causing the vibrating means to vibrate an internal wall of the esophagus which allows the laryngectomee to form speech. The air flow altering means may comprise a flap and the breath activated device may include an electric contact which activates the breath activated device when the air flow altering means is in a closed position. The electric contact may be powered by a power pack which may be located outside the laryngectomee. The means for vibrating the internal wall of the esophagus may include a transducer and the position and pressure of the transducer may be adjusted by a means disposed within the tube which may include an inflatable bladder. The adjusting means may be controlled by a control pack which may be located outside the laryngectomee. The device may further include a cannula which is removably received within the tube and the air flow altering means, breath activated device and vibrating means may be disposed upon the cannula. Lastly, the device may also include an inflatable cuff which may be inflated by an external pump.

BRIEF DESCRIPTION OF THE DRAWINGS

Various objects, features, and attendant advantages of the present invention will be more fully appreciated as the same become better understood from the following detailed description of the present invention when considered in connection with the accompanying drawings, in which.

DETAILED DESCRIPTION OF THE DRAWINGS

Figure 1:
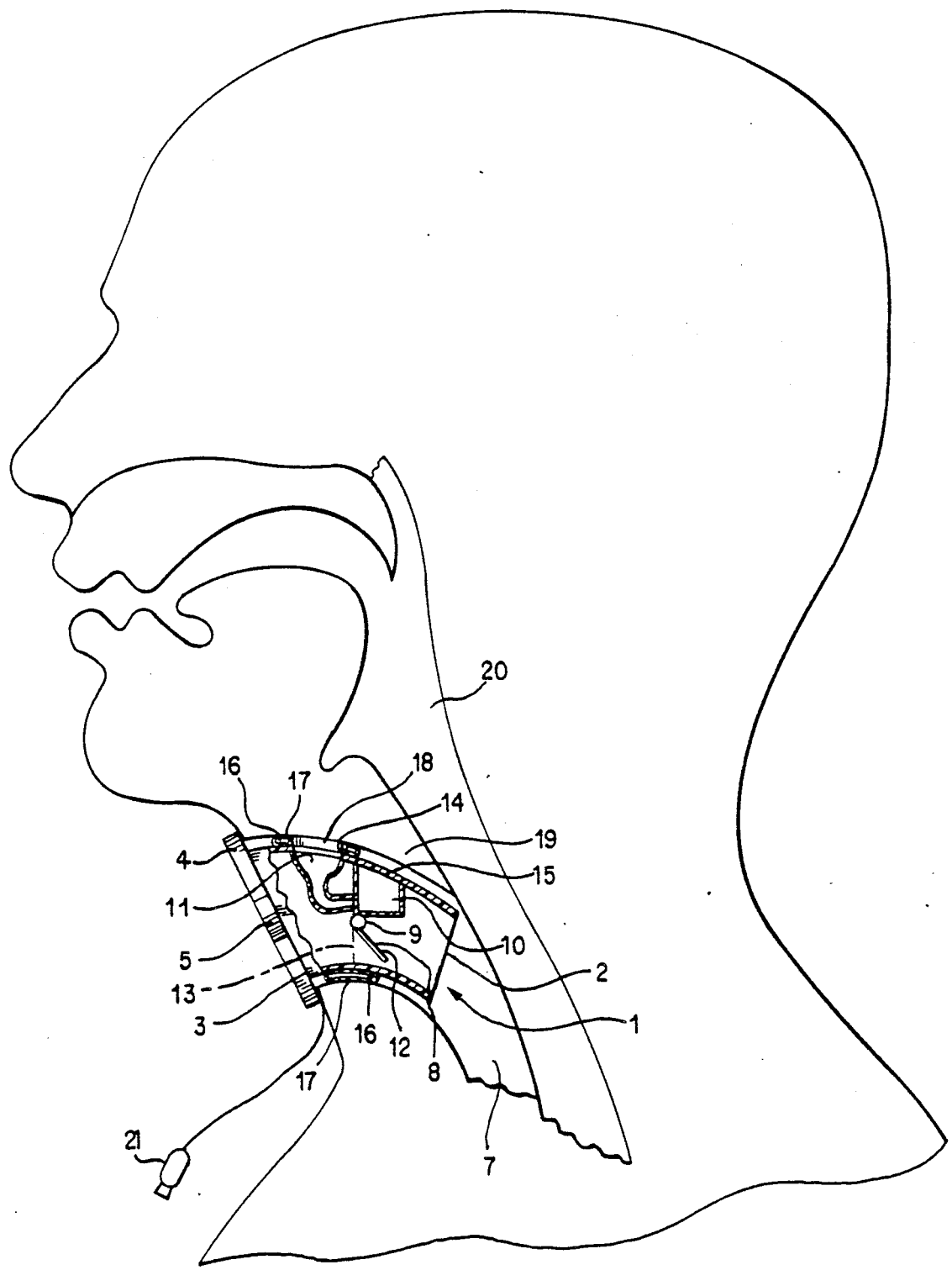
FIG. 1 is a cross-sectional view of one embodiment of the speaking tube of the present invention inserted within the trachea of a laryngectomee.
Figure 2:
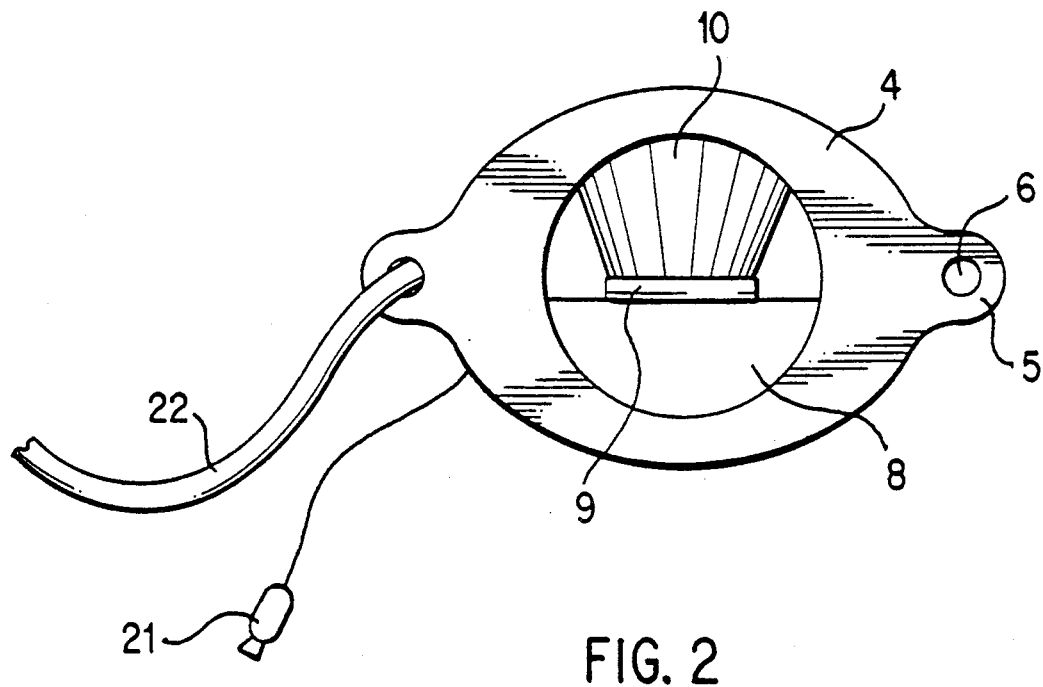
FIG. 2 is a front view of the embodiment shown in FIG. 1.

With continuing reference to the drawing figures in which similar reference numerals are used throughout the description to describe similar features of the respective embodiments, a first embodiment of the present invention which is a device for creating speech in a laryngectomee is shown in FIG. 1. The device comprises a speaking tube 1, an air flow altering means 8, a vibrating means 10 and a sound transporting means 11, each of which will now be described in greater detail. In its preferred embodiment, speaking tube 1 is a cylinder or tube. The tube is approximately two inches in length and is one-quarter inch in diameter. The tube may be constructed of surgical stainless steel or other suitable material which is biologically compatible with human tissues, non-collapsible and easily cleaned. The speaking tube 1 includes an insertion end 2 and a stoma engaging end 3. The tube is of uniform diameter and is preferably curved between the insertion end 2 and the stoma engaging end 3 to follow the natural curvature of the human trachea 7. As best seen in FIG. 2, stoma engaging end 3 is provided with a generally circular-shaped face plate 4 which includes extensions 5. Extensions 5 are disposed opposite each other at the sides of face plate 4. Each extension 5 is provided with a hole or opening 6 for receiving a tape or cord 22 which is tied or secured by any suitable fastener at the back of the laryngectomee's neck to retain the speaking tube 1 within the trachea 7.

Air flow altering means 8 is shown in the drawings as a flap, however, other suitable devices may be used so long as they serve to alter the flow of air through the tube 1. Flap 8 is disposed within the speaking tube 1 approximately mid-way between ends 2 and 3. Flap 8 is positionable between an open or first position 12 and a closed or second position 13 (shown in phantom) by means of a conventional spring or hinge 9 which is secured to flap 8 by a pin or other suitable securing means. During normal exhalation, flap 8 remains in the open position 12 and the flow of exhaled air is directed from the trachea 7 outside of the body. During more forceful exhalation, flap 8 is moved to the closed position 13 and the flow of exhaled air is directed to the vibrating means 10. Both the flap 8 and the spring or hinge 9 are constructed of surgical stainless steel or other suitable material.

Vibrating means 10, for creating vibrations within the tube 1 is positioned within the tube superior to the spring or hinge 9 and may be secured thereto by any suitable securing means. Vibrating means 10 may include a reed, spring, or narrow valve or any other device which is capable of creating vibrations when a stream of air is directed thereover. Vibrating means 10 is in direct communication with a sound transporting means which is shown in the drawings as a sound port 11. Sound port is positioned anterior to vibrating means 10 so that the vibrations traveling therethrough will contact and penetrate the upper stoma wall at the most optimum location. This optimum location, known as the "sweet spot", allows vibrations to travel through the tissue of the neck to the section of the esophagus most appropriate for speech creation. Sound port is substantially funnel shaped, the narrower end of which is in communication with vibrating means 10, while the larger end or aperture 14 opens along the upper surface 15 of speaking tube 1.

Figure 1A:
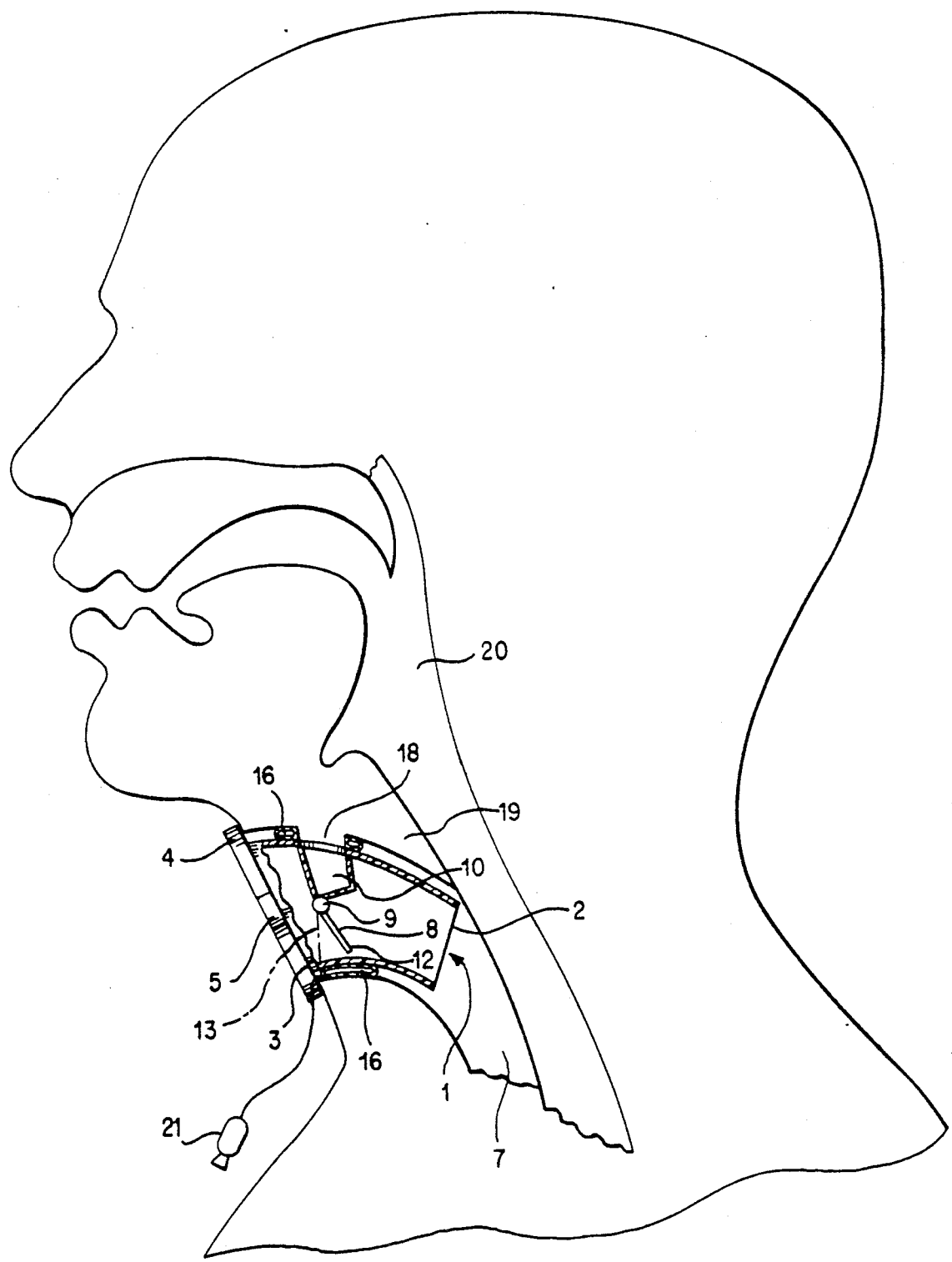
FIG. 1a is a cross-sectional view of a modified embodiment of the speaking tube of FIG. 1 inserted within the trachea of a laryngectomee.

However, as shown in the modified embodiment illustrated in FIG. 1a, sound port 11 need not be present. Vibrating means 10 may be positioned directly beneath the laryngectomee's "sweet spot". As a result, the vibrations created by vibrating means 10 travel immediately through the neck tissue under their initial strength due to the lack of vibration absorption by sound port 11. Thus, the walls of the esophagus vibrate with a great strength which allows the creation of clear, articulate speech.

Figure 3:
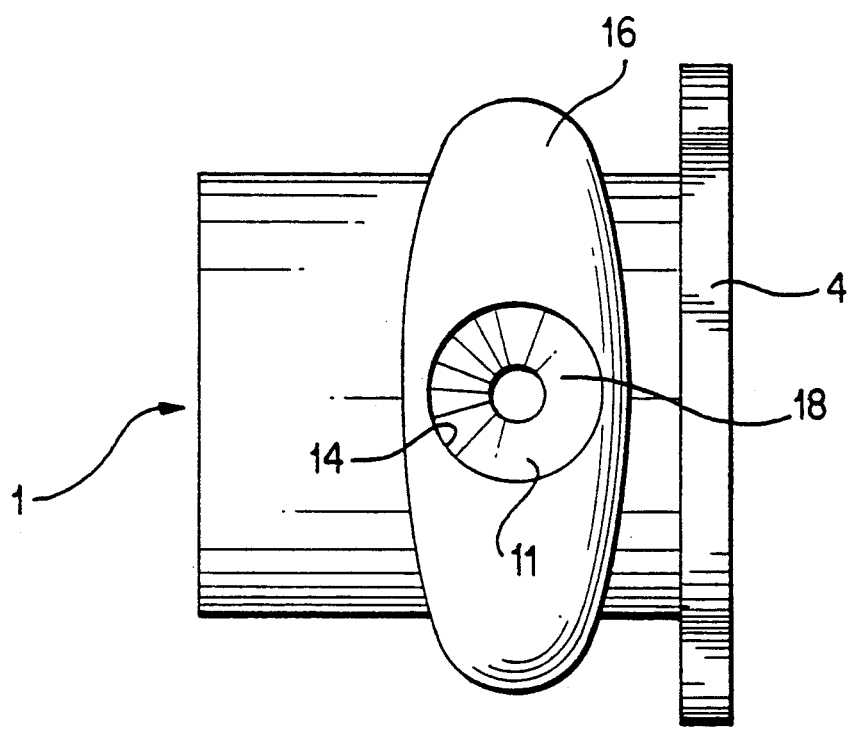
FIG. 3 is a top view thereof.

Turning now to FIG. 3, an inflatable cuff 16 is shown surrounding the outside surface of speaking tube 1. The cuff 16 is preferably positioned approximately one-quarter inch behind the face plate 4 so that the cuff, when inflated will engage with the interior walls of the stoma 17 to prevent dislodgement of the tube. Inflatable cuff 16 is provided with an aperture 18 which is positioned in substantial alignment with aperture 14 of the speaking tube. The cuff 16 is also provided with an external, removable syringe or pump 21 for inflation of cuff 16. Upon proper inflation of the cuff, that is, when the tube 1 is secure within the trachea 7 of the laryngectomee, pump 21 is disengaged from the cuff and removed. The inflatable cuff 16 is constructed of an expandable material, such as medical grade silicon, and is inflated with a suitable gaseous medium such as air.

It should be noted that the dimensions of the speaking tube provided heretofore are approximate and that the speaking tube is specifically dimensioned to fit securingly within the stoma of a male or female laryngectomee. For example, a speaking tube to be utilized by a female tends to be somewhat smaller in size in relation to a tube to be utilized by a male. However, regardless of the specific dimensions of the tube, the tube may be further secured within the stoma by inflating cuff 16.

The speaking tube of the present invention is utilized by the laryngectomee in the following manner. The insertion end 2 of speaking tube 1 is inserted into the trachea 7 through the stoma until the face plate 4 of the tube is against the throat of the laryngectomee. The speaking tube tie tapes 22 are brought to the back of the laryngectomee's neck and are tied together or are fastened in a suitable manner to secure the speaking tube within the stoma. Inflatable cuff 16 is then inflated by pump 21 to further secure the speaking tube within the trachea. The laryngectomee initiates speech by exhaling more forcefully than during normal breathing to force flap 8 from an open position 12 to a closed position 13. When the flap 8 is in the closed position 13, exhaled air is directed upward to the vibrating means 10. Air forced against or through vibrating means 10 produces vibrations which are directed through the sound port 11 to the superior wall of the stoma 17. The vibrations subsequently travel through the tissues of the neck 19 to the esophagus 20. (If the embodiment shown in FIG. 1a is utilized, the vibrations created by vibrating means 10 are directed immediately to the superior wall of the stoma where they then travel through the tissues of the neck to the esophagus 20.) As the walls of the esophagus 20 vibrate, the laryngectomee is able to form speech by using normal oral, labial and glossal articulation. Flap 8 returns to open position 12 when normal breathing is resumed and breath is directed out of the stoma.

Figure 4:
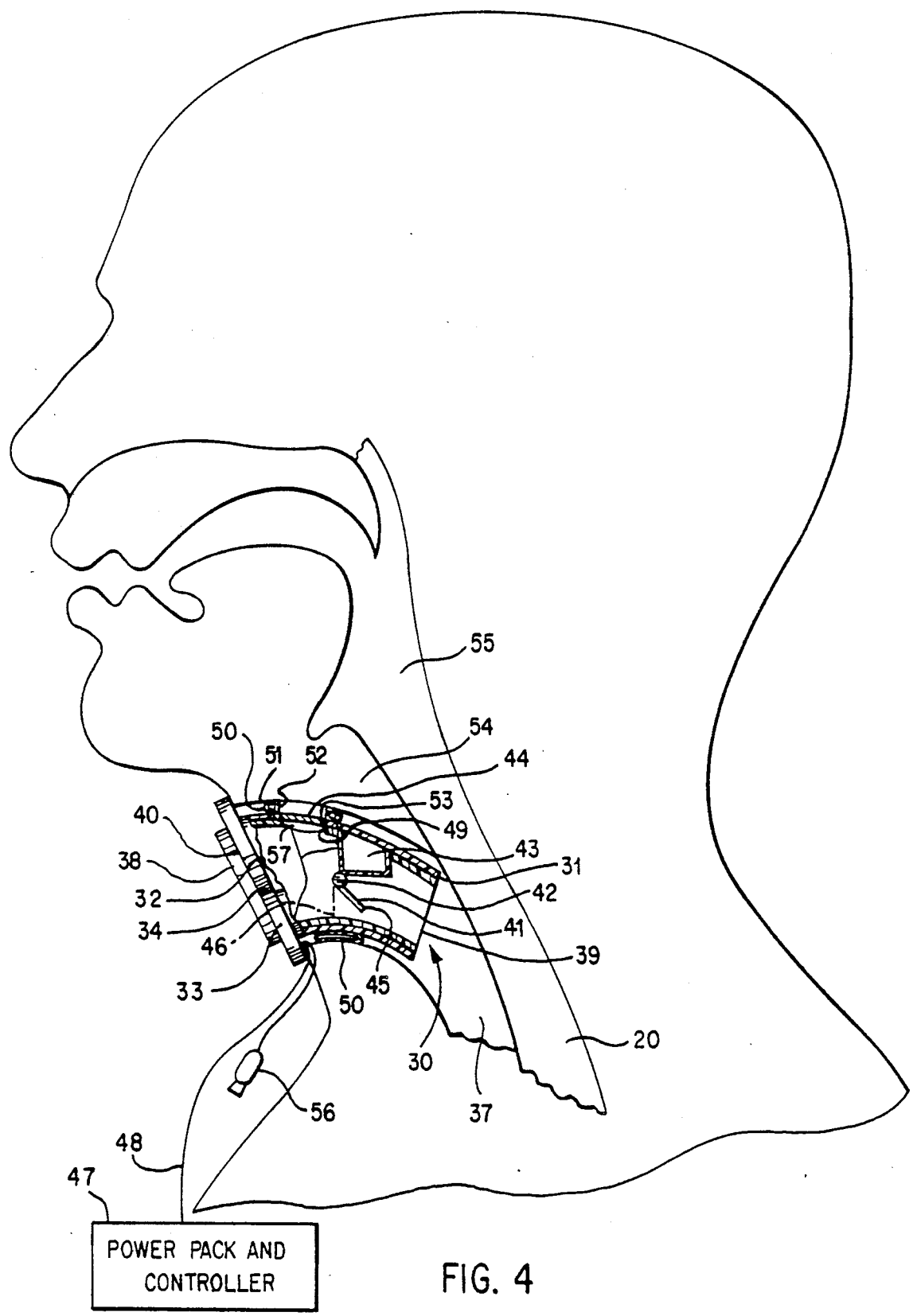
FIG. 4 is a cross-sectional view of a second embodiment of the speaking tube of the present invention inserted within the trachea of a laryngectomee.
Figure 6:
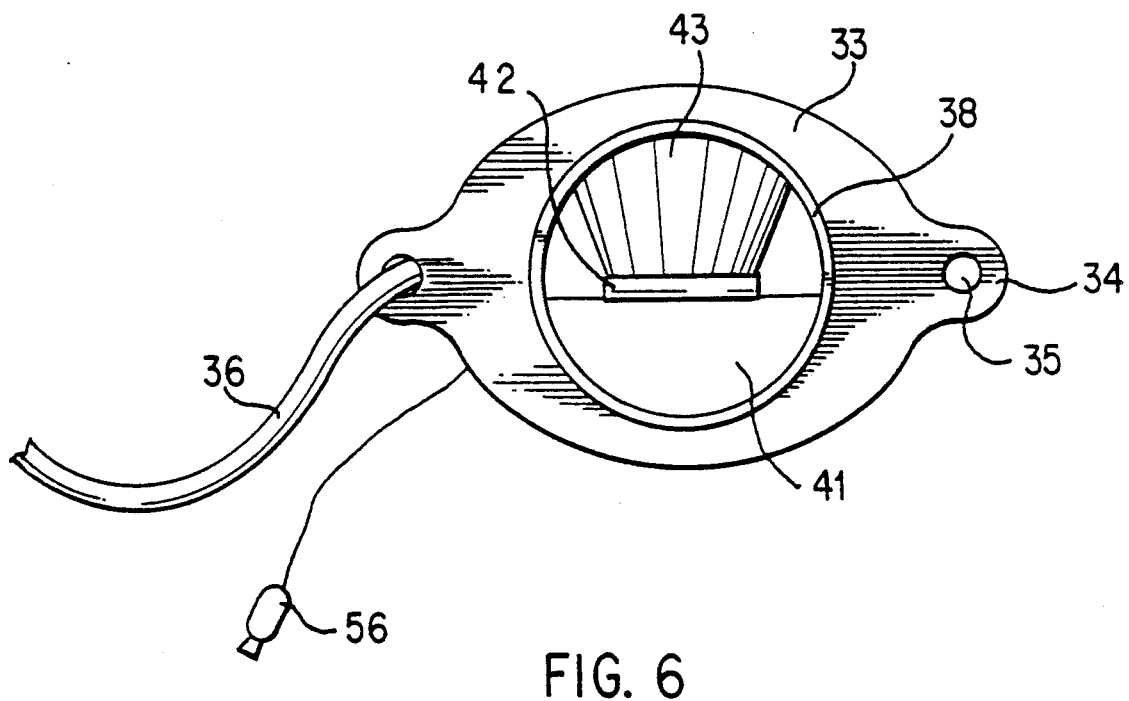
FIG. 6 is a front view thereof.

A second embodiment of the speaking tube of the present invention is an electro-mechanical device for allowing a laryngectomee to form speech and is shown generally at 30 in FIG. 4. The electro-mechanical speaking tube 30 takes the same general form as the mechanical speaking tube 1 shown in FIG. 1. The speaking tube 30 is also cylindrical in shape and of uniform diameter, is preferably approximately two inches in length and is constructed of surgical stainless steel or other suitable material. Tube 30 is curved in a radius similar to tube 1 to follow the interior contour of trachea 37. The speaking tube 30 includes an insertion end 31 and a stoma engaging end 32. The tube 30 is fitted at its stoma engaging end 32 with a generally circular-shaped face plate 33 which includes extensions 34. As best seen in FIG. 6, the extensions 34 are disposed opposite each other at the sides of face plate 33. Each extension 34 is provided with a hole or opening 35 for receiving a tape or cord 36 which is tied or fastened at the back of the laryngectomee's neck to retain the speaking tube 30 within the trachea 37 of the laryngectomee.

The speaking tube 30 is provided with an inner tube or cannula 38 which is slidably received within speaking tube 30. Inner cannula 38 includes an insertion end 39 and a face plate engaging end 40. The diameter of inner cannula 38, uniform throughout its length, is slightly smaller than the uniform diameter of outer speaking tube 30 to allow the inner cannula 38 to be inserted into outer speaking tube 30. The inner cannula 38 is also preferably constructed of surgical stainless steel or other suitable material which is biologically compatible with human tissues.

With continuing reference to FIG. 4, the inner cannula 38 is generally comprised of an air flow altering means 41, a spring or hinge 42, a breath detecting device 43 and a transducer 44. The air flow altering means 41 may include a flap or other suitable device which is constructed of surgical stainless steel or other biologically compatible material and is disposed midway between ends 39 and 40 of inner cannula 38. Similar to flap 8 of FIGS. 1–3, flap 41 is positionable between an open or first position 45 and a closed or second position 46 by means of the spring or hinge 42. Hinge 42 is also preferably constructed of surgical stainless steel and is secured to flap 41 by a pin or other conventional securing means. During normal exhalation by the laryngectomee, flap 41 remains in open position 45 and the flow of exhaled air is directed outside the laryngectomee's body. During more forceful exhalation, the flap 41 is forced into the closed position 46 (shown in phantom).

A breath activated device or electrical contact 43 is positioned within the inner cannula 38 superior to the spring or hinge 42 and is secured thereto by any suitable securing means, such as screws. Electrical contact 43 is preferably metal. A corresponding electric contact, also preferably of metal, is disposed on spring or hinge 42 such that when flap 41 is forced into closed position 46, the two elements 42 and 43 contact and act as a switch to trigger an electric current which is generated by an external power pack 47 (although not shown, the power pack may also be disposed within the interior of inner cannula). The electric current generated by power pack 47 travels along an electrically conductive wire 48 to provide power to transducer 44. Transducer 44 preferably comprises an electrodynamic oscillator (such as that disclosed in U.S. Pat. No. 4,272,647 to Veit, et al., the disclosure of which is incorporated herein in its entirety by reference) which creates vibrations. The transducer 44 is positioned upon the superior or upper portion of the inner cannula 38 (anterior of the breath detecting device 43) and is in direct alignment with aperture 49 formed in the inner cannula.

Figure 5:
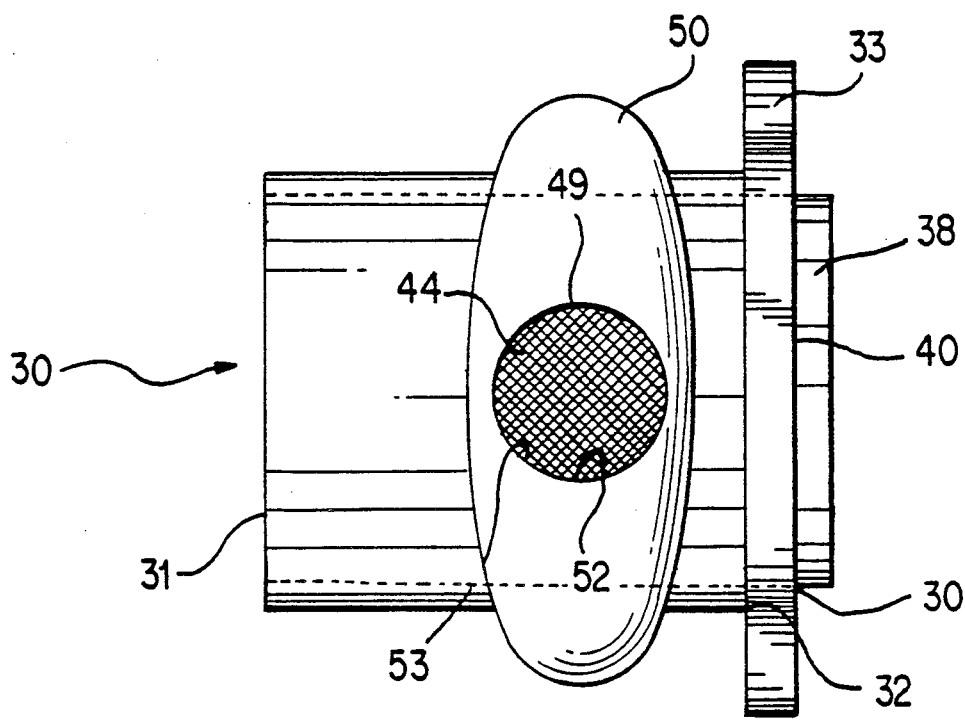
FIG. 5 is a top view thereof.

As best seen in FIG. 5, an inflatable cuff 50 surrounds the outside of speaking tube 30. Cuff 50 is preferably positioned approximately one-quarter inch behind face plate 33 so that the cuff, when inflated, may securingly engage with the walls of the stoma 51. Inflatable cuff 50 is provided with an aperture 52 which is positioned to be in direct alignment with inner cannula aperture 49 and speaking tube aperture 53 to allow the vibrations produced by transducer 44 to travel through the tissues of the neck 54 to the esophagus 55.

Inflatable cuff 50 is provided with an external, removable inflation syringe or pump 56 which inflates cuff 50 with a suitable gaseous medium, such as air, to secure tube 30 within trachea 37 of the laryngectomee. When the tube is secure within the trachea, pump 56 is disengaged from the cuff and removed. Inflatable cuff 50 is constructed in the same manner as cuff 16 described previously in FIG. 1. To remove tube 30 from the trachea, pump 56 is reengaged or connected to cuff 50 to deflate or release the gaseous medium from the cuff. Pump 56 is then removed from the deflated cuff, and tube 30 is removed from the trachea of the laryngectomee.

An inflatable air bladder 57 (FIG. 4) is disposed within inner cannula 38 beneath transducer 44. Inflatable air bladder 57 serves to adjust the position and pressure of the transducer 44 against the stoma wall 51. The inflation of air bladder 57 is adjusted by a suitable control which may be located within power pack 47.

This embodiment of the speaking tube of the present invention is utilized by the laryngectomee in the following manner. The insertion end 31 of speaking tube 30 is inserted into the trachea 37 through the stoma until the face plate 33 of the tube is against the throat of the laryngectomee. The speaking tube tie tapes or cords 36 are inserted through the holes or openings 35 and are brought to the back of the laryngectomee's neck and are tied together or fastened in a suitable manner to secure the speaking tube within the trachea. The insertion end 39 of inner cannula 38 is inserted into the speaking tube 30 until the face plate engaging end 40 of inner cannula 38 is against the face plate 33. The inflatable cuff 50 is then inflated by inflation pump 56 to further secure the speaking tube within the trachea 37. During normal breathing, flap 41 is in its open position 45 and air is allowed to pass through the stoma to the trachea and lungs of the laryngectomee. The laryngectomee initiates speech by exhaling more forcefully than during normal breathing to force the air flow altering device or flap 41 into the closed position 46. The movement of the attached metal spring or hinge 42 against breath activated device 43 acts as a switch to send power from the power pack 47 to the transducer 44. The transducer 44 creates vibrations which travel to the stoma wall 51 through apertures 49, 52 and 53. The vibrations travel through the tissue of the neck 54 to the esophagus 55. When the vibrations reach the esophagus, the walls of the esophagus vibrate and the laryngectomee is able to form speech by using normal oral, labial and glossal articulation. If the position or pressure of transducer 44 against the stoma wall should need to be adjusted so that it contacts the laryngectomee's "sweet spot" (i.e. the optimum location along the stoma wall for creating speech), the inflatable air bladder 57 is inflated by the controller until the appropriate pressure and position is obtained.

When normal breathing is resumed, the flap returns to open position 45 and the movement of the hinge 42 against the breath activated device 43 interrupts power from the power pack 47 to cut off power to the transducer 44.

One advantage of inner cannula 38 is that it allows easy cleaning of the interior elements of the invention. Furthermore, although not shown, an inner cannula comprised of an air flow altering means, a vibrating means, and a sound transporting means may be received within the speaking tube shown in FIG. 1.

The invention which is intended to be protected herein should not be construed as limited to the particular forms disclosed, as these are to be regarded as illustrative rather than restrictive. Variations and changes may be made by those skilled in the art without departing from the spirit of the invention. Accordingly, the foregoing detailed description should be considered exemplary in nature and not limited to the scope and spirit of the invention as set forth in the attached claims.

What is claimed is:

1. A device for creating speech in a laryngectomee comprising:
   a tube adapted to be received within the trachea of said laryngectomee, said tube including an insertion end and a stoma engaging end;
   a tissue vibrating means positioned between said insertion end and said stoma engaging end of said tube for causing the tissue of the esophagus to vibrate; and
   an air flow altering means disposed within said tube for altering the flow of air during exhalation, said altering means positionable between an open position wherein the flow of air is directed outside the body and a closed position wherein the flow of air is directed to said vibrating means,
   wherein when said flow of air is directed to said tissue vibrating means, said vibrations cause an internal wall of the esophagus to vibrate, which allows said laryngectomee to form speech.

2. A device as set forth in claim 1, wherein said altering means for altering the flow of air comprises a flap.

3. A device as set forth in claim 1, wherein said vibrating means for creating said vibrations is selected from the group consisting of a reed, a spring, a transducer and a narrow valve.

4. A device as set forth in claim 1, further comprising a cannula which is removably received within said tube.

5. A device as set forth in claim 4, wherein said air flow altering means and said vibrating means are disposed on said cannula.

6. A device as set forth in claim 1, wherein said tube is constructed of stainless steel.

7. A device as set forth in claim 1, further comprising a sound transporting means for transporting said vibrations to said internal wall of said esophagus of said laryngectomee.

8. A device as set forth in claim 7, wherein said transport means includes a sound port.

9. A device as set forth in claim 1, further comprising a securing means for securing said tube within the trachea of the laryngectomee.

10. A device as set forth in claim 9, wherein said securing means includes an inflatable cuff.

11. A device as set forth in claim 10, wherein said cuff is inflatable by an external pump.

12. A device for creating speech in a laryngectomee comprising:
    a tube adapted to be received within the trachea of said laryngectomee, said tube including an insertion end and a stoma engaging end;
    a means for vibrating an internal wall of the esophagus positioned within said tube between said insertion end and said stoma engaging end;
    an air flow altering means received within said tube for altering the flow of air during exhalation, said altering means positionable between an open position and a closed position; and a breath activated device received within said tube;

wherein said breath activated device activates said vibrating means when said air flow altering means is in a closed position causing said vibrating means to vibrate said internal wall of said esophagus, which allows said laryngectomee to form speech.

13. A device as set forth in claim 12, wherein said air flow altering means comprises a flap.

14. A device as set forth in claim 12, wherein said breath activated device includes an electric contact, wherein said breath activated device is activated when said air flow altering means is in a closed position.

15. A device as set forth in claim 12, wherein said means for vibrating the internal wall of said esophagus comprises a transducer.

16. A device as set forth in claim 12, further comprising a cannula which is removably received within said tube and wherein said air flow altering means, said breath activated device and said vibrating means are disposed on said cannula.

17. A device as set forth in claim 12, further comprising an inflatable cuff disposed about said tube; and an external pump for inflating said inflatable cuff.

18. A device as set forth in claim 15, further comprising a means disposed within said tube for adjusting the position and pressure of said transducer.

19. A device as set forth in claim 18, wherein said adjustment means includes an inflatable bladder.

20. A device as set forth in claim 18, further comprising a control pack for controlling said adjusting means.

21. A device as set forth in claim 14, further comprising a power pack for supplying power to, said electric contact.

22. A device as set forth in claim 20, wherein said control pack is locatable outside of the laryngectomee.

23. A device as set forth in claim 21, wherein said power pack is locatable outside of the laryngectomee.

* * * * *